(12) United States Patent
Grasruck et al.

(10) Patent No.: US 7,778,454 B2
(45) Date of Patent: Aug. 17, 2010

(54) METHOD AND APPARATUS FOR DETERMINING THE CONCENTRATION OF A SUBSTANCE IN A BODY MATERIAL BY MEANS OF MULTI-ENERGY COMPUTED TOMOGRAPHY

(75) Inventors: Michael Grasruck, Erlangen (DE); Bernhard Krauss, Altdorf (DE)

(73) Assignee: Siemens Aktiengesellschaft, Munich (DE)

( * ) Notice: Subject to any disclaimer, the term of this patent is extended or adjusted under 35 U.S.C. 154(b) by 842 days.

(21) Appl. No.: 11/710,934

(22) Filed: Feb. 27, 2007

(65) Prior Publication Data

US 2007/0217570 A1 Sep. 20, 2007

(30) Foreign Application Priority Data

Feb. 28, 2006 (DE) .................. 10 2006 009 222

(51) Int. Cl.
*G06K 9/00* (2006.01)
(52) U.S. Cl. .............. 382/128; 382/130; 382/131; 382/132; 382/154; 382/284; 378/97; 378/98; 378/9; 378/22; 378/53; 600/425; 600/458
(58) Field of Classification Search .......... 382/128, 382/130, 131, 132, 154, 173, 284; 378/97, 378/98.9, 6, 19, 22, 4, 5; 600/425, 458
See application file for complete search history.

(56) References Cited

U.S. PATENT DOCUMENTS 6,973,158 B2 * 12/2005 Besson ................. 378/16
6,987,833 B2 * 1/2006 Du et al. ................. 378/98.9
7,319,739 B2 * 1/2008 Heismann ................ 378/62
7,352,885 B2 * 4/2008 Eberhard et al. .......... 382/131
7,440,603 B2 * 10/2008 Eberhard et al. .......... 382/131
7,599,465 B2 * 10/2009 Walter et al. ............. 378/4
2004/0101088 A1 5/2004 Sabol et al.

* cited by examiner

*Primary Examiner*—Wes Tucker
*Assistant Examiner*—Nancy Bitar
(74) *Attorney, Agent, or Firm*—Harness, Dickey & Pierce, P.L.C.

(57) ABSTRACT

At least one embodiment of the present application relates to a method and/or an apparatus for determining the concentration of a substance in a body material that is composed of two different material components in an unknown ratio. In an embodiment of the method, two computed tomography pictures from which two image data records are reconstructed are recorded in conjunction with two different spectral distributions of the x-radiation. The x-ray attenuation values for each voxel of the two image data records are decomposed into three material components. The decomposition is performed on the assumption that the x-ray attenuation value $x_M$ of the body material without the substance is composed of the x-ray attenuation values $x_{M1}$, $x_{M2}$ of the first and second material component in accordance with the following equation: $x_M = f \cdot x_{M1} + (1-f) \cdot x_{M2}$, f being a volume fraction of the first material component in the body material. The concentration of the substance is then determined for each voxel of interest on the basis of the decomposition. The concentration can be determined reliably in a simple way with the aid of an embodiment of the present method and/or an embodiment of the associated apparatus.

19 Claims, 2 Drawing Sheets

METHOD AND APPARATUS FOR DETERMINING THE CONCENTRATION OF A SUBSTANCE IN A BODY MATERIAL BY MEANS OF MULTI-ENERGY COMPUTED TOMOGRAPHY

PRIORITY STATEMENT

The present application hereby claims priority under 35 U.S.C. §119 on German patent application number DE 10 2006 009 222.8 filed Feb. 28, 2006, the entire contents of which is hereby incorporated herein by reference.

FIELD

Embodiments of the present invention generally relate to a method for determining the concentration of a substance in a body material, such as one that is composed of two different material components in an unknown ratio for example. For example, embodiments of the method may relate to one in which two computed tomography pictures of the body material are recorded with the aid of a multi-energy computer tomograph in conjunction with two different spectral distributions of the x-radiation, and from the two computed tomography pictures are reconstructed two image data records from which the concentration of the substance for each voxel of interest is determined. Embodiments of the invention also generally relate to an apparatus, such as one designed for carrying out the method for example.

One field of application of at least one embodiment of the present invention generally relates to determining a contrast agent concentration in the body material of a human or animal patient, in particular the contrast agent concentration in the liver.

BACKGROUND

Two different techniques have been known so far for determining this contrast agent concentration by means of computed tomography (CT). Thus, it is possible before and after administering contrast agent to record a computed tomography picture of the body area in which the contrast agent concentration is to be measured. After the two CT images obtained thereby are registered, they are subtracted from one another in order to obtain the rise in the x-ray attenuation values for each pixel or each voxel that is caused by the contrast agent. This rise in the x-ray attenuation values is proportional to the concentration of the contrast agent. However, the computed tomography pictures at different times that are required in this case can entail registration and/or movement artifacts that can lead to a defective determination. When use is made of a contrast agent that collects only slowly in the body material, there is a need, in addition, to observe an undesirably long waiting time between the two computed tomography pictures.

The second known technique employs the use of a multi-energy computer tomograph for simultaneously recording two computed tomography pictures with a different spectral distribution of the x-radiation, that is to say a different x-ray energy. In one variant of this technique, the image data records for two x-ray energies are firstly reconstructed separately from one another. Subsequently, the measured x-radiation values for each voxel are decomposed into the molecular density of two base materials (2-material decomposition), of which one base material constitutes the contrast agent. The two equations resulting from the decomposition can then be used to determine for each voxel the two unknowns, the concentrations of the two base materials. However, for many body materials this technique does not yield satisfactory results, since the decomposition is difficult to predict for all the material components contained in the body material. Thus, the application of this technique for determining the contrast agent concentration in the liver, which generally also contains relatively large fractions of fat, leads to a mixture of the two base materials that is difficult to interpret.

SUMMARY

In at least one embodiment, the present invention includes a method and/or an apparatus for quantitatively determining the concentration of a substance, in particular a contrast agent concentration, in a body material which enables a more reliable determination of the concentration in a simple way.

In at least one embodiment of the present method, two computed tomography pictures of the body material are recorded with the aid of a multi-energy computer tomograph, in particular with the aid of a so-called dual energy computer tomograph, in conjunction with two different spectral distributions of the x-radiation. The recording with the two different x-ray energies is preferably performed here simultaneously. Two image data records that include x-ray attenuation values x are reconstructed from the measured data of the computed tomography pictures in a known way. Here, x-ray attenuation values can be understood both as the attenuation coefficients $\mu$ and as values derived therefrom, such as the CT value.

The x-ray attenuation values x for each voxel of interest of the two image data records are decomposed in the present method into x-ray attenuation values of three material components. These three material components are the two different material components of the body material, and the substance whose concentration is to be determined. The two different material components of the body material need not, of course, be chemically pure materials in this case, but can also constitute material mixtures.

The decomposition of the x-ray attenuation values is performed in the present method on the assumption that the x-ray attenuation value $x_M$ of the body material without the substance is composed of the x-ray attenuation values $x_{M1}$, $x_{M2}$ of the first and second material component in accordance with the following equation:

$$x_M = f^* x_{M1} + (1-f)^* x_{M2},$$

f being a volume fraction of the first material component in the body material. The concentration of the substance is then determined for each voxel of interest on the basis of this decomposition. This is possible since there are respectively yielded for each voxel two equations (corresponding to the two image data records) with a total of two unknowns, the volume fraction f of the first material component, and the concentration c of the substance enriched in the body material.

In an example refinement of an embodiment of the method, the concentration of the substance is therefore also determined by solving this system of equations of the following two equations:

$$x_{E1} = c^* x_{KM,E1} + f^* x_{M1,E1} + (1-f)^* x_{M2,E1}$$

$$x_{E2} = c^* x_{KM,E2} + f^* x_{M1,E2} + (1-f)^* x_{M2,E2},$$

in which $x_{E1/E2}$ corresponds to the x-ray attenuation values from the two image data records in conjunction with the different spectral distributions and/or energies E1, E2 of the x-radiation, and c corresponds to the concentration of the substance in the body material. The x-ray attenuation values $x_{M1}$ and $x_{M2}$ in conjunction with the different x-ray energies E1, E2 are known, and can be taken from a table, for example.

The same holds for the x-ray attenuation value $x_{KM}$ of the substance to be determined. This can also be determined in advance, if appropriate, by way of a separate calibration measurement, for example using a water phantom.

At least one embodiment of the present method and/or the associated apparatus employ the realization that in reality many materials of approximately constant density occur in the human and animal body. Starting from this property, it is assumed that mixtures of two materials are also not represented with arbitrary x-ray attenuation values in a CT picture. It should prove possible to substantiate this experimentally for liver tissue, for example. The CT value of liver tissue decreases linearly with an increasing fraction of stored fat.

Furthermore, it is known that the difference between the x-ray attenuation values for different tube voltages of the computer tomograph, that is to say in conjunction with different x-ray energies, is a linear function of the fat content. This relationship can also be transferred to other body materials, and is utilized in at least one embodiment of the present invention and the associated apparatus in that the equation specified in patent claim 1 is taken into account when decomposing the x-ray attenuation values.

The method and the apparatus of at least one embodiment are therefore suitable for a simple and direct measurement and/or determination of the concentration of a substance in a body material which in many instances supplies more reliable results than the 2-material decomposition previously applied. The substance whose concentration is to be determined should, however, in this case cause a substantial rise in the x-ray attenuation values in the CT pictures. This obtains straight away in the case of determining contrast agent concentrations.

The contrast agent concentration in the liver is determined in an example application of at least one embodiment of the present method and/or of the associated apparatus. Here, fat and liver tissue constitute the two material components that are used in the method for decomposition. Despite further materials typically occurring in the liver, the general classification in a mixture of fat and tissue leads nevertheless to a correct determination of the contrast agent concentration.

In an example refinement of at least one embodiment of the present method and/or the associated apparatus, there is calculated from at least one of the image data records and from the previously determined concentrations a rise in the x-ray attenuation values in the corresponding image data record for each voxel or voxel of interest that is caused by the substance. This rise in the x-ray attenuation values is subsequently displayed as an image in which the regions enriched with the substance are then to be detected with the aid of a gray tone assigned to the respective concentration of the substance. In a further advantageous refinement, in which a rise in the x-ray attenuation values is likewise calculated, the calculated rise is subtracted from the x-ray attenuation values of the corresponding image data record such that an image can be obtained without a contribution to the substance and displayed, this being denoted below as a virtual native image.

At least one embodiment of the present apparatus includes a multi-energy computer tomograph that is designed for simultaneously recording two computed tomography pictures of the body material in conjunction with different x-ray energies and/or different spectral distributions of the x-radiation, an image reconstruction unit for reconstructing two image data records from the two computed tomography pictures, as well as a determination module for determining and outputting the concentration of the substance for each voxel of interest. In at least one embodiment of the present apparatus, the determination module is designed to carry out the decomposition and calculation steps of at least one embodiment of the present method. Thus, in particular, the x-ray attenuation values x for each voxel of interest in the two image data records are decomposed by the determination module into x-ray attenuation values of the three material components in order to determine the concentration of the substance therefrom on the assumption made in the case of at least one embodiment of the method.

At least one embodiment of the present method and/or the associated apparatus can be used in this case not only for determining a contrast agent concentration in the liver, but also for determining a contrast agent concentration or a concentration of other substances in other body materials if these body materials can be approximately represented as a mixture of two material components on the assumption made in at least one embodiment of the present method. This is also the case, for example, with mixtures of water and an ideal soft tissue. The two material components of the relevant body material need not be chemically pure materials in this case, since even in the case of the liver the material components of the liver tissue already contain water. The stepwise replacement of one material component by another in conjunction with an unchanged content of a third component can also be represented as a mixture of only two material components of known density.

A particular application of at least one embodiment of the present method and/or of the associated apparatus relates to the distinction of bone and contrast agent in a body material. In addition to the contrast agent, use is made as material components for this purpose of the components of tissue (similar to blood and red bone marrow) and ideal bones. In principle, only the ideal mixtures of tissue and contrast agent and tissue and bone should occur in the body. It is true that in reality the presence of yellow bone marrow, for example, can cause deviations from these ideal mixtures to occur. However, even in these instances at least one embodiment of the present method and/or the associated apparatus can be used to obtain the desired separation between bones and regions containing contrast medium.

BRIEF DESCRIPTION OF THE DRAWINGS

The present method and the associated apparatus are explained briefly once again below with the aid of an example embodiment in con junction with the drawings, without restricting the scope of protection prescribed by the patent claims. Here:

DETAILED DESCRIPTION OF THE EXAMPLE EMBODIMENTS

Figure 1:
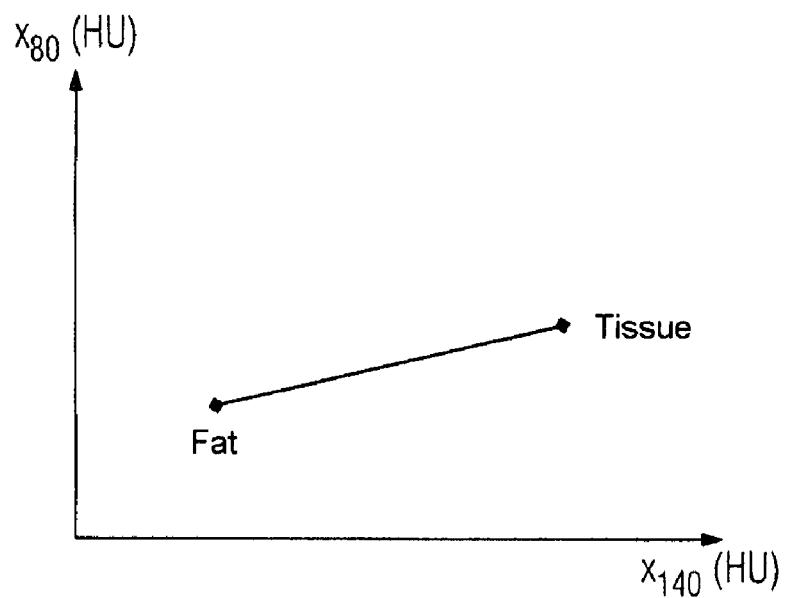
FIG. 1 shows a first diagram for explaining the relationships in the case of an embodiment of the present method.

The terminology used herein is for the purpose of describing particular embodiments only and is not intended to be limiting of the present invention. As used herein, the singular forms "a","an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the term "and/or" includes any and all combinations of one or more of the associated listed items.

An example embodiment of the present method and the associated apparatus are explained in more detail once again below with the aid of determination of the contrast agent concentration in the liver of a patient. It may be substantiated experimentally from liver tissue that the mixtures of pure liver tissue and fat cannot occur with its desired CT value in computed tomography pictures with constant x-ray energy or a constant x-ray spectrum. It is known that the CT value of liver tissue decreases linearly when fat is stored. A drop of approximately 15 HU per 10% fat content is specified in this regard in the literature.

Moreover, it is known that the difference between, for example, a CT value for a tube voltage of 80 kV and a CT value for a tube voltage of 140 kV is a linear function of the fat content. It is assumed on the basis of this fact that the following linear dependence of the CT value x as a function of the fat content f is approximately valid for both tube voltages:

$$x = f * x_{fat} + (1-f) * x_{tissue}.$$

Here, $x_{fat}$ and $x_{tissue}$ denote the CT values of the pure materials, which depend on the tube voltage. If the CT value for the tube voltage of 80 kV is plotted against the CT value for the tube voltage of 140 kV, all the possible mixtures of fat and tissue must lie on a straight line. This is illustrated in FIG. 1.

Figure 2:
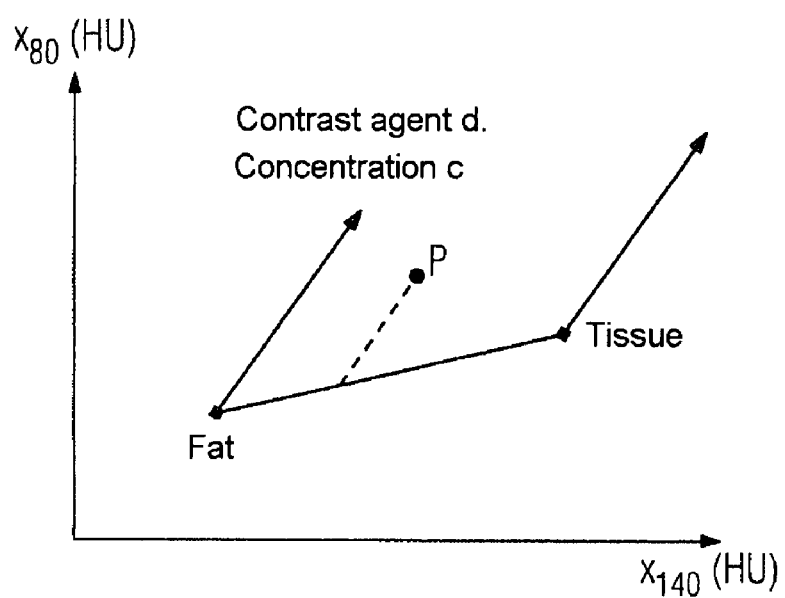
FIG. 2 shows a second diagram for explaining the relationships in the case of an embodiment of the present method.

In this model, the addition of contrast agent has the effect of raising the two CT values. Since, even in the case of low concentrations, contrast agent itself causes a substantial absorption, it holds approximately that the CT value increases linearly with the concentration of the added contrast agent, the proportionality constant not being dependent on the material, that is to say on the specific fat/tissue mixture. The diagram illustrated in FIG. 1 can therefore be expanded in accordance with FIG. 2. Thus, the fat content f and the contrast agent concentration c can therefore be calculated for each point in this diagram.

Taking a desired point P, for example, the fat content f and the concentration c can be determined by means of the indicated projection of this point onto the straight line between fat and tissue. Furthermore, the rise in the CT value $\Delta x_{KM}$ ($= c * x_{KM}$) can be determined from this diagram both for the tube voltage of 80 kV and for the tube voltage of 140 kV. A comparable diagram is also yielded when the method is applied to a body material that contains bone and tissue. In this case, the fat is replaced in the diagram of FIG. 2 by the tissue, and the tissue is replaced by the bone material.

The materials of muscle tissue and water likewise lie approximately on the fat-tissue straight line in the case of liver examination. Consequently, all materials typically occurring in the liver are therefore classified as fat and tissue with the aid of the parameters for fat and tissue, although the contrast agent concentration c must always be correctly determined nevertheless. By correctly determining the contrast agent concentration, it is possible to prepare a virtual native image by subtracting the rise in CT value caused by the contrast agent from the respective image.

Figure 3:
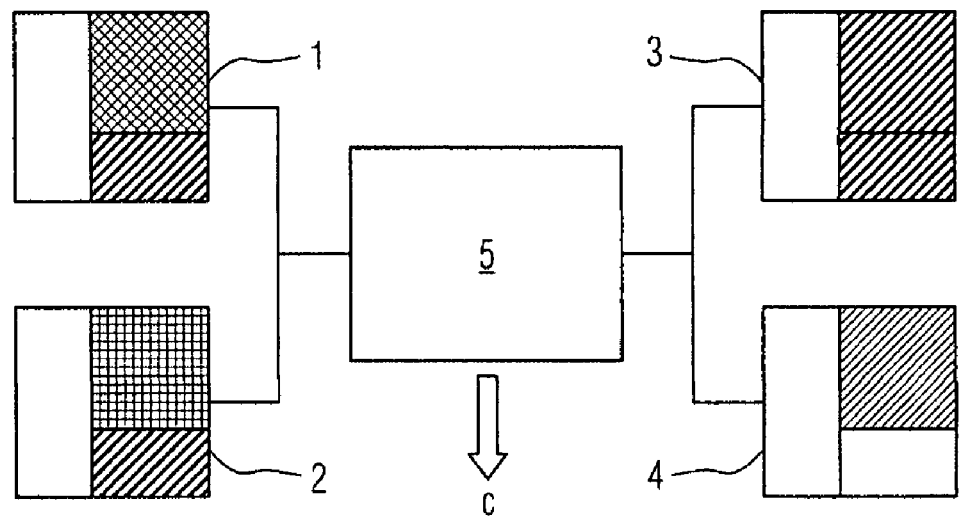
FIG. 3 shows an example of the method sequence in the case of an embodiment of the present method.

FIG. 3 shows an example of this mode of procedure in the case of the present method. A dual energy computer tomograph is used to record simultaneously two CT pictures for different tube voltages of 80 kV and 140 kV, and the corresponding CT images 1, 2 are reconstructed from the measured data. The x-ray attenuation values included in the CT images 1, 2 are correspondingly decomposed in accordance with an embodiment of the present method, as indicated in the figure, in order to determine the concentration of the contrast medium in a spatially resolved fashion. A contrast agent image 3, on the one hand, and a virtual native image 4, on the other hand, are calculated and displayed on the basis of this decomposition.

Figure 4:
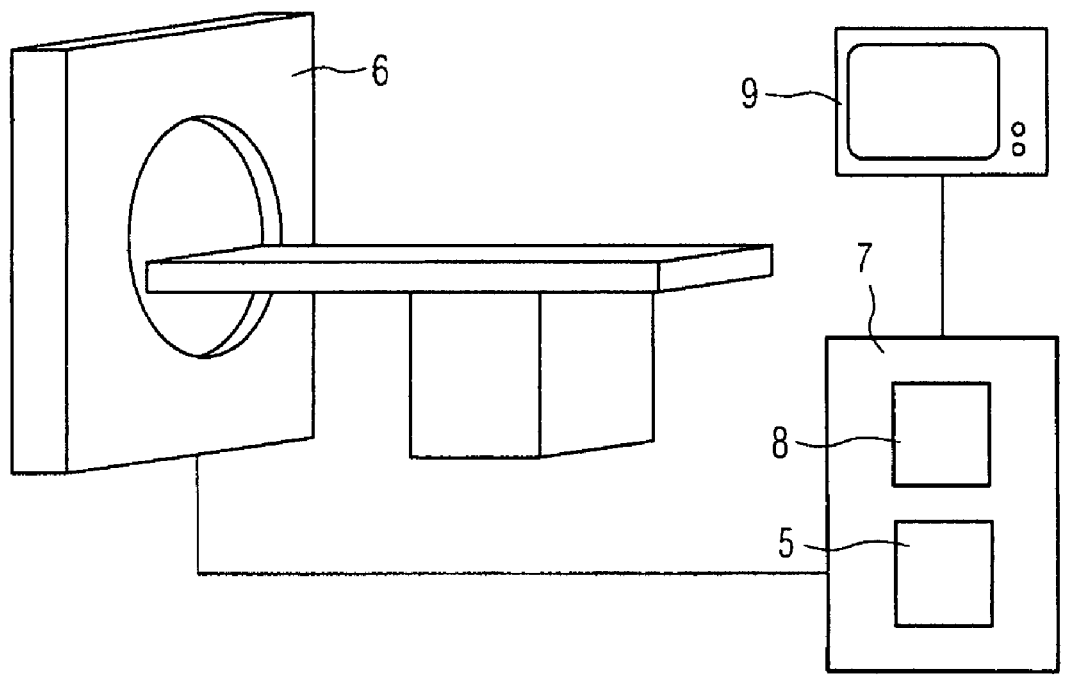
FIG. 4 shows a schematic of an example of an embodiment of the present apparatus.

The entire operation of decomposing and calculating the contrast agent and native images is performed in the determination module 5 of a computer tomograph 6 that is illustrated schematically in FIG. 4. This computer tomograph 6 includes an image computer 7 in which the image reconstruction unit 8 and the determination module 5 are implemented. The images output by the determination module 5 are displayed on a monitor 9 connected to the image computer 7.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining the concentration of a substance in a body material that is composed of two different material components in an unknown ratio, comprising:
   recording two computed tomography pictures of the body material with the aid of a multi-energy computer tomograph in conjunction with two different spectral distributions of the x-radiation;
   reconstructing two image data records from the two computed tomography pictures, the image data records including x-ray attenuation values x;
   decomposing the x-ray attenuation values x for each voxel of interest of the two image data records into x-ray attenuation values of three material components of which a first and a second constitute the two different material components of the body material and a third constitutes the substance, wherein the decomposition is performed on the assumption that the x-ray attenuation value $x_M$ of the body material without the substance is composed of the x-ray attenuation values $x_{M1}, x_{M2}$ of the first and second material component in accordance with the following equation:

$$x_M = f \ast x_{M1} + (1-f) \ast x_{M2},$$

f being a volume fraction of the first material component in the body material; and
   determining the concentration of the substance for each voxel of interest on the basis of the decomposition.

2. The method as claimed in claim 1, wherein the concentration of the substance is determined by solving the following systems of equations for the different spectral distributions of the x-radiation E1, E2 for f and c:

$$x_{E1} = c \ast x_{KM,E1} + f \ast x_{M1,E1} + (1-f) \ast X_{M2,E1}$$

$$x_{E2} = c \ast x_{KM,E2} + f \ast x_{M1,E2} + (1-f) \ast x_{M2,E2}$$

$X_{E1,E2}$ corresponding to the x-ray attenuation values from the two image data records in conjunction with the different spectral distributions of the x-radiation, and c corresponding to the concentration of the substance in the body material.

3. The method as claimed in claim 1, wherein the concentration of a contrast agent in the body material is determined.

4. The method as claimed in claim 1, wherein the concentration of a contrast agent in the liver is determined, the first material component constituting fat, and the second material component constituting tissue.

5. The method as claimed in claim 1, wherein a rise in the x-ray attenuation values in at least one of the image data records that is caused by the substance is determined and displayed as image.

6. The method as claimed in claim 1, wherein a rise in the x-ray attenuation values in at least one of the image data records that is caused by the substance is determined, and a native image is calculated by subtraction from the x-ray attenuation values of this image data record and displayed.

7. The method as claimed in claim 1, wherein the two computed tomography pictures are recorded simultaneously.

8. An apparatus for determining the concentration of a substance in body material that is composed of two different material components in an unknown ratio, the apparatus comprising:
   a multi-energy computer tomograph, to simultaneously record two computed tomography pictures of the body material in conjunction with different spectral distributions of the x-radiation;
   an image reconstruction unit to reconstruct two image data records from the two computed tomography pictures; and
   a determination module to decompose the x-ray attenuation values x for each voxel of interest of the two image data records into x-ray attenuation values of three material components of which a first and a second constitute the two different material components of the body material, and a third constitutes the substance, wherein the decomposition is performed on the assumption that the x-ray attenuation value xM of the body material without the substance is composed of the x-ray attenuation values $x_{M1}, x_{M2}$ of the first and second material component in accordance with the following equation:

$$x_M = f \ast x_{M1} + (1-f) \ast x_{M2},$$

f being a volume fraction of the first material component in the body material, to determine the concentration of the substance for each voxel of interest on the basis of the decomposition, and output the determine the concentration.

9. The apparatus as claimed in claim 8, wherein the determination module is designed to carry out the determination of the concentration of the substance by solving the following system of equations for the different spectral distributions of the x-radiation El, E2 for f and c:

$$x_{E1} = c \ast x_{KM,E1} + f \ast x_{M1,E1} + (1-f) \ast x_{M2,E1}$$

$$x_{E2} = c \ast x_{KM,E2} + f \ast x_{M1,E2} + (1-f) \ast x_{M2,E2}$$

$x_{E1/E2}$ corresponding to the x-ray attenuation values for the two image data records in conjunction with the different spectral distributions of the x-radiation, and c corresponding to the concentration of the substance in the body material.

10. The apparatus as claimed in claim 8, wherein the determination module is designed to determine a rise in the x-ray attenuation values in at least one of the image data records caused by the substance, and to output the determined rise to an image display device as an image.

11. The apparatus as claimed in claim 8, wherein the determination module is designed to determine a rise in the x-ray attenuation values in at least one of the image data records caused by the substance, and to calculate a native image by subtracting the x-ray attenuation values of this image data record, and to output the calculated a native image an image display device.

12. The method as claimed in claim 2, wherein the concentration of a contrast agent in the body material is determined.

13. The method as claimed in claim 2, wherein the concentration of a contrast agent in the liver is determined, the first material component constituting fat, and the second material component constituting tissue.

14. The method as claimed in claim 2, wherein a rise in the x-ray attenuation values in at least one of the image data records that is caused by the substance is determined and displayed as image.

15. The method as claimed in claim 2, wherein a rise in the x-ray attenuation values in at least one of the image data records that is caused by the substance is determined, and a native image is calculated by subtraction from the x-ray attenuation values of this image data record and displayed.

16. The method as claimed in claim 2, wherein the two computed tomography pictures are recorded simultaneously.

17. A computer readable medium including program segments for, when executed on a computer device, causing the computer device to implement the method of claim 1.

18. The apparatus as claimed in claim 9, wherein the determination module is designed to determine a rise in the x-ray attenuation values in at least one of the image data records caused by the substance, and to output the determined rise to an image display device as an image.

19. The apparatus as claimed in claim 9, wherein the determination module is designed to determine a rise in the x-ray attenuation values in at least one of the image data records caused by the substance, and to calculate a native image by subtracting the x-ray attenuation values of this image data record, and to output the calculated a native image an image display device.

* * * * *